(12) United States Patent
Brauckman et al.

(10) Patent No.: US 6,821,296 B2
(45) Date of Patent: Nov. 23, 2004

(54) DEVICE FOR DELIVERING A RADIOACTIVE AND/OR DRUG DOSAGE ALONE OR IN CONNECTION WITH A VASCULAR STENT

(75) Inventors: Richard A. Brauckman, Cumming, GA (US); Jack C. White, Alpharetta, GA (US); Bruce Smith, Lithonia, GA (US)

(73) Assignee: Theragenics Corporation, Buford, GA (US)

( * ) Notice: Subject to any disclaimer, the term of this patent is extended or adjusted under 35 U.S.C. 154(b) by 0 days.

(21) Appl. No.: 09/874,580

(22) Filed: Jun. 5, 2001

(65) Prior Publication Data

US 2002/0019662 A1 Feb. 14, 2002

Related U.S. Application Data

(60) Provisional application No. 60/208,904, filed on Jun. 5, 2000.

(51) Int. Cl.[7] ................................................ A61F 2/06
(52) U.S. Cl. ........................................ 623/1.42; 600/3
(58) Field of Search ............................. 623/1.42, 1.44, 623/1.15; 600/3, 8

(56) References Cited

U.S. PATENT DOCUMENTS

| | | |
|---|---|---|
| 5,059,166 A | 10/1991 | Fischell et al. |
| 5,176,617 A | 1/1993 | Fischell et al. ................ 600/3 |
| 5,199,939 A | 4/1993 | Dake et al. |
| 5,342,283 A | 8/1994 | Good |
| 5,503,613 A | 4/1996 | Weinberger |
| 5,540,659 A | 7/1996 | Teirstein |
| 5,618,266 A | 4/1997 | Liprie |
| 5,797,948 A | 8/1998 | Dunham |
| 5,863,285 A | 1/1999 | Coletti |
| 5,879,282 A | 3/1999 | Fischell et al. |
| 6,149,574 A * | 11/2000 | Trauthen et al. ................ 600/3 |
| 6,152,869 A * | 11/2000 | Park et al. ...................... 600/3 |
| 6,192,271 B1 * | 2/2001 | Hayman ....................... 604/21 |
| 6,193,746 B1 * | 2/2001 | Strecker .................... 623/1.13 |
| 6,261,320 B1 * | 7/2001 | Tam et al. ................. 623/1.15 |
| 6,287,249 B1 * | 9/2001 | Tam et al. ...................... 600/3 |
| 6,293,899 B1 * | 9/2001 | Sioshansi et al. .............. 600/3 |
| 6,447,439 B1 * | 9/2002 | Vallana et al. ................. 600/3 |

OTHER PUBLICATIONS

"Effect of Iridium 192 Radiation on Thromboatherosclerotic Plaque in the Rabbit Aorta," Meyer Friedman, MD and Sanford O. Byers, PhD, Arch Path—vol. 80, Sep. 1965, Page Nos. 285–290.

"The Antiatherogenic Effect of Iridium upon the Cholesterol–fed Rabbit," Meyer Friedman, Leland Felton and Sanford Byers with the Technical Assistance of Warren Hayashi, Clarence Omoto and Ashley Tam, Journal of Clinical Investigation, vol. 43, No. 2, 1964, Page Nos. 185–192.

* cited by examiner

*Primary Examiner*—Michael H. Thaler
(74) *Attorney, Agent, or Firm*—Knoble Yoshida & Dunleavy LLC

(57) ABSTRACT

A stent for insertion into a vessel of a body and used in connection with a foil sheet, where the foil sheet comprises a radioactive material, is described. The stent and foul sheet are positioned so that the radioactive material in the foil sheet can deliver a desired dosage to an prescribed area, thereby reducing the distance for delivering the radioactive dose. The radioactive material may comprise carrier-free palladium 103. The foils screen may further comprise a shielding lay on the side for directing the dosage. A method for placing the stent and foil into a vessel of a body is also described.

17 Claims, 4 Drawing Sheets

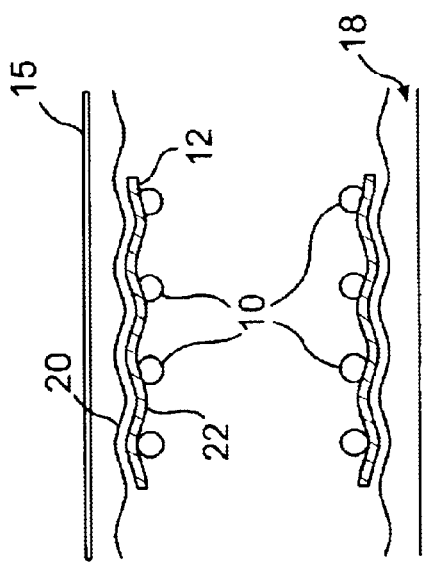
*FIG. 4*
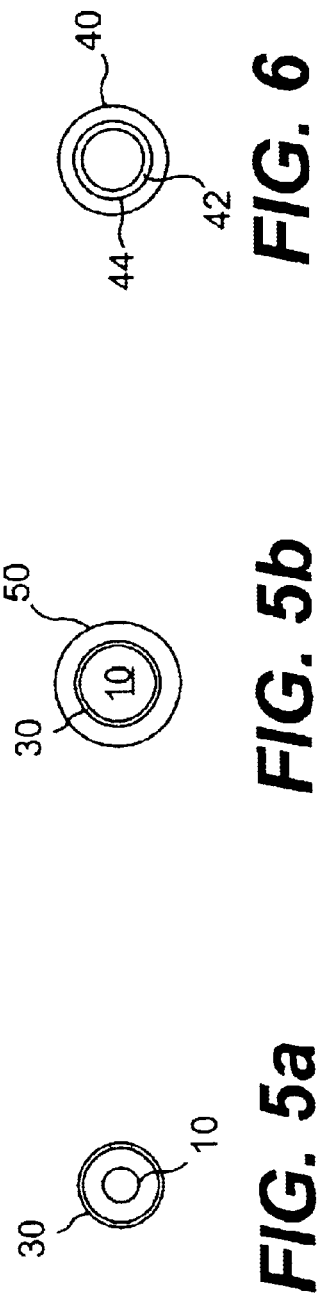
*FIG. 5a*
*FIG. 5b*
*FIG. 6*

DEVICE FOR DELIVERING A RADIOACTIVE AND/OR DRUG DOSAGE ALONE OR IN CONNECTION WITH A VASCULAR STENT

RELATED APPLICATION DATA

This application claims the benefit of U.S. Provisional patent application No. 60/208,904, filed Jun. 5, 2000, under 35 U.S.C. §119(e).

FIELD OF THE INVENTION

The present invention relates generally to a method and device for delivering a radioactive dose and/or drugs alone or in combination with the deployment of a stent.

BACKGROUND OF THE INVENTION

Various types of brachytherapy treatments employ radioactive material, such as treatments designed to combat cancer or to prevent scar issue build-up. One manner of brachytherapy involves inserting devices comprising radioactive materials into a body (e.g., a human body) to provide localized irradiation.

Once such use of radioactive materials is to prevent restenosis in a blood vessel. Intra-vascular stents have been used to prevent restenosis after angioplasty procedures. Intra-vascular stents may suffer from the drawback of excessive scar tissue growth (e.g., intimal hyperplasia) at the site of the angioplasty and/or the stent due to trauma to the vessel which results from a combination of the angioplasty and stenting procedures, thereby reducing the long-term effectiveness of the procedure.

One attempt to solve this problem has been to incorporate radioactive material into a stent, thereby irradiating vessel tissue at the stent site to reduce tissue growth at the site. Such stents, however, may be difficult and costly to manufacture. Incorporating radioactive material in such a stent may for example, require coating the stent with a layer of radioactive material and binding the radioactive material to the stent. Coating the stent may be difficult due to the stent structure, since many stents have a helical or other complex geometric structure in order to provide support to the vessel without occluding flow through the vessel.

Additionally, radioactive stents may use a sealing layer to adhere the radioactive material to the stent, and/or to provide the stent with certain physical properties desirable for a stent (e.g., coil spring stents). A sealing layer may reduce the effective dose of radioactivity by blocking or absorbing a portion of the radioactivity. This may require use of larger amounts of costly radioactive material. Further, sealing layers may have an adverse impact on the uniformity of the radiation dosage delivered by the stents. For example, unless such sealing layers are uniform, thicker areas of the sealing layer may reduce the dosage delivered by the radioactive material more than thinner areas of the sealing layer, thereby resulting in a non-uniform dosage.

When using radioactive material to treat tissue, it important for the radioactive material to be as close to the tissue as possible, thereby allowing the minimum amount of radioactive material to be used, to provide an effective dose and to minimize the dosage delivered to other tissues. Using sealing layers or other coatings to attach the radioactive material to the stent results in the radioactive material being placed further away from the vessel than desired.

These and other drawbacks exist.

SUMMARY OF THE INVENTION

An object of certain embodiments of the present invention is to overcome these and other drawbacks in existing systems and methods.

Another object of certain embodiments of the invention is to provide a device for use in connection with a vascular stent to radiate and/or deliver drugs to a localized area in a vessel in a body.

Another object of certain embodiments of the invention is to provide a device for implantation in vessel to irradiate and/or deliver drugs to a localized area.

Additional objects and advantages of the invention will be set forth in part in the description, or may be learned by practice of the invention.

To achieve these objects and in accordance with the purpose of the invention, as embodied and broadly described herein, the present invention provides, in one embodiment, a foil sheet comprising a radioactive material useful in association with a stent for delivery of a localized radiation dosage.

In another embodiment, the present invention relates to the combination of a stent and a foil sheet comprising a radioactive material. The stent and foil sheet are positioned so that the radioactive material in the foil sheet can deliver a localized radiation dosage to a prescribed area.

The accompanying drawings, which are incorporated in and constitute a part of this specification, illustrate an embodiment of the invention and, together with the description, serve to explain the principles of the invention, but in no way constitute the entire invention and are not to be construed as limits the invention in any way.

BRIEF DESCRIPTION OF THE DRAWINGS

FIG. 4 is a cross-sectional view of a vessel with a foil sheet according to an embodiment of the invention shown in combination with a stent.

FIGS. 5a and 5b are cross-sectional views of an expandable tubular sheath in combination with a stent according to another embodiment of the invention.

FIG. 6 is a cross-sectional view of another embodiment of the present invention where the foil sheet is attached to the inner surface of the stent.

DETAILED DESCRIPTION OF THE PREFERRED EMBODIMENTS

Figure 1A:
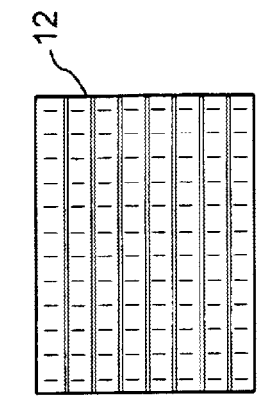
FIGS. 1a and 1b are a cross-sectional view and a front view of the foil sheet, respectively, according to an embodiment of the invention.

Reference will now be made in detail to the present preferred embodiments of the invention, examples of which are illustrated in the accompanying drawings in which like reference characters refer to corresponding elements.

In general, the present invention relates to a method and device for delivering a radioactive and/or drug dosage to a localized area of the body either alone or in combination with a vascular stent. Various embodiments of the invention are described in detail below.

Figure 1B:
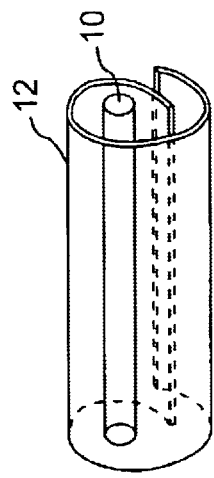

FIGS. 1a and 1b are a cross-sectional view and a front view of a foil sheet 12 which may be used, for example, in association with a stent according to an embodiment of the invention. Foil sheet 12 may be fabricated as a flat sheet of material. Foil sheet 12 is designed to be placed adjacent the outer surface of a stent 10 by surrounding the stent 10 with the foil sheet 12. Stent 10 may be any conventional stent used within a vessel of a body, such as an artery, bile duct, or other vessel.

According to a specific embodiment of the invention, the stent 10 is preferably an expandable stent 10, such as a spring wire, helical coil stent. In this embodiment, foil sheet 12 is preferably formed in the shape of a coil for use as shown in FIG. 1*a*. The expandable stent 10 is a generally tubular structure which is unobstructed throughout its length. As the stent 10 is expanded, the diameter of the stent 10 increases to cause the outer surface of expandable stent 10 to contact the inner surface of the vessel within the body. Stents 10 are generally employed to provide support to such vessels in order to hold them open until they heal in a way that they will remain as open as possible to allow passage of bodily fluids therethrough.

In use, the coiled foil sheet 12 is placed around the expandable stent 10 when it is in its contracted position. Stent 10 is then inserted to the desired location and expanded in the usual manner. Since foil sheet 12 surrounds stent 10, expansion of stent 10 results in contact between the outer surface of stent 10 and foil sheet 12 thereby causing the foil sheet 12 to expand, for example, by uncoil. In this manner, both the stent 10, and the foil sheet 12 may be expanded together such that the foil sheet 12 is trapped between the outer surface of stent 10 and the wall of the vessel to thereby provide close contact between foil sheet 12 and the wall of the vessel as shown in FIG. 4.

Coiling foil sheet 12 enables a sufficient amount of foil sheet 12 to be located around stent 10 to ensure that the entire outer surface of stent 10 is covered by foil sheet 12 when stent 10 is in the fully expanded position without any gaps at the ends of the foil sheet 12. This she enables irradiation of the entire wall of the vessel.

Alternatively, a foil sheet 12 can be fabricated from a stretchable or expandable material. In this embodiment an expandable tubular member 30 is formed from a foil sheet 12 as shown, for example, in FIG. 5*a*. The tubular member 30 is placed around the expandable stint 10 and, upon expansion of the stent as shown in FIG. 5*b*, the foil sheet 12 stretches to expand and fit tightly around the outer surface of expandable stent 10 whereby it is trapped against the inner wall 50 of the vessel as in the previous embodiment.

Tubular member 30 may have any suitable cross-sectional configuration for the particular stent 10 with which it will be employed. For example, circular, oval, elliptical, square, rectangular or polygonal cross-sectional configurations may be used, among others. According to an embodiment of the invention, foil sheet 12 may be deployed after the angioplast procedure is completed and before a stent 10 is deployed. For example, the foil sheet 12 may be deployed in the treatment area and the stent 10 subsequently inserted within foil sheet 12. Alternatively, foil sheet 12 may be inserted in a device used for deploying stents, such as a catheter, and then the stent 10 may be deployed in position within the foil sheet 12 in the delivery device such that the stent 10 and foil sheet 12 are delivered together in the appropriate arrangement relative to one another to the treatment zone.

According to another embodiment of the invention, a foil sheet 42 may be located inside the stent 40. Preferably, foil sheet 42 is affixed in any suitable manner to the inner surface 44 of stent 40 as shown in FIG. 6 such then when the stent 40 is expanded, foil sheet 42 expands with it to remain attached to the inner surface 44 of stent 40. As the foil sheet 42, and stent 40 are expanded, the outer surface of the stent 42 contacts the interior wall of the vessel and the foil sheet 42 is brought into close proximity with the area to be irradiated. Other, similar embodiments may also be employed.

Figure 2:
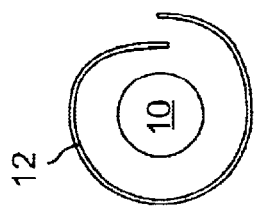
FIG. 2 is a top view of a foil sheet in a flat configuration according to an embodiment of the invention.

FIG. 2 illustrates foil sheet 12 in a flat configuration as it would be when first fabricated, for example, prior to being coiled or formed into a tubular member 30. By the term "foil sheet" is meant a sheet, screen or web of material which has a radioactive material on at least a portion of one surface thereof. According to an embodiment of the invention, foil sheet 12 may be a screen having a porous open weave. The screen may be woven using any conventional type of weave.

The foil sheet 12 may be fabricated using a biocompatible fiber. More particularly, the substrate can be formed from a non-toxic metallic, non-metallic, polymeric, or ceramic material. The substrate can be a fiber, ribbon, mesh, patch, film, or the like. Further, the substrate can be deformable, solid, hollow, porous, or even sufficiently porous to allow for tissue growth therein.

In one embodiment, the substrate may be formed from a memory alloy such as the nickel-titanium alloy nitinol. Such memory alloys can be deformed in use and then returned to their original shape by a thermal treatment process. This may provide advantages such as reusability of the foil sheet 12 in cases where the radioactive material can be regenerated by proton or neutron bombardment, example.

In one preferred embodiment, the substrate can be a metallic sheet formed from a high atomic number metal or alloy such as iridium, platinum, gold, tantalum, tungsten, or lead. Additionally, any lower atomic weight metal or alloy which is satisfactorily visualized on radiographs may be used including molybdenum, indium lithium, silver, copper, and stainless steel. Alternatively, when only magnetic resonance imaging of the delivery device is clinically desirable, the substrate can be a non-magnetic material, formed from, for instance, aluminum, carbon, diamond, graphite or various polymers.

In another embodiment, the substrate can be a thin film, fiber, ribbon, mesh, patch, or the like formed from polymeric materials The polymeric material is preferably be selected from the group consisting of polyvinyl chloride, polysulfones, cellulose esters, nylon, Dacron™, polyesters, polyolefins, polyurethanes, polyamides, polyimides and modified versions of one or more of these materials, as well as any other polymeric materials known by a skilled person to be suitable for this purpose. It should be noted that radiation can have degrading effects on certain polymeric materials, as is known in the art. Particularly preferred polymeric materials for forming the substrate include radiation-stabilized polypropylene materials such as those disclosed in U.S. Pat. Nos. 5,122,593 and 5,140,073, which are hereby incorporated by reference for the purpose of describing these particular materials.

Optionally, the polymeric materials forming the substrate can include absorbent materials to enhance adherence of the radiation source material to the substrate. Suitable materials may include activated carbon powder, activated charcoal, or ion exchange resins. Common ion exchange resins include sulfonated polystyrene resins, methylene-sulfonic phenolic resins, phosphoric polystyrene resins, polystyrene resins containing quartenary ammonium groups, pyridinium polystyrene resins, epoxy-polyamine resins containing tertiary and quaternary ammonium groups, iminodiacetic polystyrene resins, and polystyrene resins containing polyamine groups.

In yet another embodiment, the substrate can be formed from a biodegradable polymeric material such as polyethylene glycol or polyethylene glycol-polyethylene oxide block copolymer. Further, the substrate can be formulated as a flexible material using of any of the above mentioned polymeric materials, if desired. For example, the substrate can be in the form of an elastomer, gel, hydrogel or foamed material.

According to one embodiment of the invention, radioactive material may be mixed with the substrate material before the substrate is formed. According to another embodiment of the invention, the radioactive material may be applied, for example as a coating, to the already fabricated substrate.

According to an embodiment of the invention, palladium$^{103}$ ("Pd-103") is preferably used as the radioactive material in foil sheet 12, although other known, radioactive materials suitable for treatment of humans or animals, such as iodine-125, palladium-103, strontium-90, ruthenium-106, phosphorus-32, samarium-145, iridium-192, cobalt-60, radioactive vanadium-48 and yttrium-90 may be employed. The radioactive source may be selected based on the specific needs of the particular treatment process, the half-life, the amount of radiation required and other parameters.

The radiation source material preferably comprises carrier-free Pd-103, although reactor grade Pd-103 may also be employed Reactor grade Pd-103 may be prepared in any suitable, conventional manner known to persons skilled in the art such as by activation of palladium metal or by fabrication in a nuclear reactor. One disadvantage of reactor grade Pd-103 is that it may contain other undesirable radioactive palladium isotopes such as Pd-109 which emit potentially harmful types of radiation. Reactor grade Pd-103 can be fabricated to minimize such impurities. Nevertheless, in some applications, particularly those where irradiation will occur close to a vital internal organ, it may be desirable to avoid use of reactor grade Pd-103 for this reason.

Carrier-free radioactive source materials, on the other hand, can be made as highly pure materials which contain essentially no undesirable radioactive isotopes in addition to the desired isotope. Hence, by the term, "carrier-free palladium" is meant that the radioactive source material is fabricated in a particle accelerator such that it contains essentially no other isotopes of the source material other than the desirable isotope.

To exemplify one process of preparing a carrier-free radioactive source material, a process for making carrier-free Pd-103 is detailed below. In accordance with the present invention, carrier-free Pd-103 can preferably be prepared in a particle accelerator as follows. A target for use in the charged particle accelerator is prepared by depositing rhodium metal onto a suitable substrate such as a copper or a silver substrate. The rhodium target thus prepared is then placed in a charged particle accelerator such as a cyclotron and bombarded with protons or deuterons. The energy of the impacting particle is chosen so that for all practical purposes the only Pd atoms created on the rhodium target are Pd-103, that is, the Pd-103 is carrier-free.

The rhodium metal containing the carrier-free Pd-103 is then placed in a hot cell wherein the rhodium metal is removed from the substrate by, for example, etching with $HNO_3$. The removal is preferably accomplished by mechanically disrupting the continuity of the rhodium layer on the substrate as by perforating the surface with a sharply pointed impact tool. The exposed (i.e. non-deposit-containing) substrate surface is covered to protect it and the perforated target immersed in a $HNO_3$ bath. A solution containing rhodium flakes results, which is filtered to recover the solid rhodium flake containing Pd-103. The recovered rhodium flakes are rinsed on the filter and the flakes together with the filter are placed in a crucible and heated to decompose the filter leaving the rhodium metal flakes containing the Pd-103.

The rhodium metal flakes thus obtained are then partially dissolved in molten $NaHSO_4$ and the resulting $NaHSO_4$/rhodium flake mixture is dissolved in dilute HCl which provides soluble rhodium salts dissolved in dilute HCl. This procedure is normally repeated several times so as to dissolve any remaining rhodium metal containing carrier-free Pd-103.

In a preferred embodiment, the radiation source material Her comprises a diluent The diluent can be added to the radioactive source material before or after purifcation For instance, preferred diluents for radioactive Pd-103 are non-radioactive palldium or rhodium metal and mixtures thereof, usually in the form of a soluble salt such as $PdCl_2$. Palladium metal is particularly preferred because palladium metal will have the same affinity for the anion exchange column as the Pd-103. As a result, it can be added as a diluent prior to purification and can be co-purified along with the carrier-free Pd-103.

Although the diluent may ,normally be considered an undesirable additive in a low energy emitting radiation source due to self-shielding effects, its addition in accordance with the present invention has been found to be advantageous in several respects. Foremost, the added diluent can serve to promote strong adhesion of the radiation source material to the substrate, thereby helping to form a layer which is substantially physiologically inert, i.e. which will not allow the radioactive material to be mobilized into the circulation of a patient being treated.

The diluent may also help to add sufficient mass to the radioactive source material to facilitate its handling, particularly when carrier-free source material is employed. In this manner, the radioactive source material can, for example, be applied more uniformly to the substrate than would have been possible in the absence of a diluent.

Also, the addition of diluent provides the ability to adjust the specific activity of the radiation source material with the objective of adjusting its self-shielding to a known value thus facilitating the manufacture of a radiation source delivery device with an accurately predetermined therapeutic or apparent activity. Thirdly, if further purification of the radiation source material is necessary, the presence of the diluent can, in some cases, help to reduce loss of radiation source material during the purification process. Diluents are particularly useful when carrier-free radioactive source materials are employed since such materials may be difficult to handle without dilution due to the relatively small mass of material used to provide the desired radiation dose.

The amount of diluent added, therefore, will vary depending principally upon the amount of radioactive source material which is available. The amount of diluent added, therefore, will vary depending principally upon the amount of radioactive source material available. Preferably, from about 0.1 mg to about 100 mg of diluent per millicurie of radioactive source material area can be used More preferably, from about 1 mg to about 50 mg of diluent per millicurie of radioactive source material is employed. Such amounts of diluent can ensure uniformity of the radioactive source material in the radiation delivery device and can promote adherence of the radiation source material to the substrate.

If design considerations, e.g., the desired mass or therapeutic activity of the delivery device, so allow, nuclear reactor produced radioactive source material can be added as a diluent to carrier-free radioactive source material, and vice-versa, particularly in cases where it may be desirable to adjust the specific activity of the radiation source material.

According to another embodiment of the invention, foil sheet 12 may permit delivery of various types of drugs. In one embodiment, foil sheet 12 may include only a drug and no radioactive material. By way of example, a foil sheet 12 may contain radioactive material and one or more drugs for treatment of, for example, intimal hyperplasia This embodiment may enable excessive tissue growth to be treated more effectively with a combination of treatments.

Foil sheet 12 may be fabricated to contain drugs according to known manners of fabricating devices for delivering drugs within a body (e.g., a human body). According to an embodiment of the invention, a foil sheet 12 includes a radioactive material in a manner described above. Further, foil sheet 12 includes drugs which are incorporated into foil sheet 12 by covering the outer portion of a foil sheet 12 with a coating containing the desired drug. Substrates and drug delivery systems known to those of skill in the art may be used in the practice of the present invention.

Figure 3B:
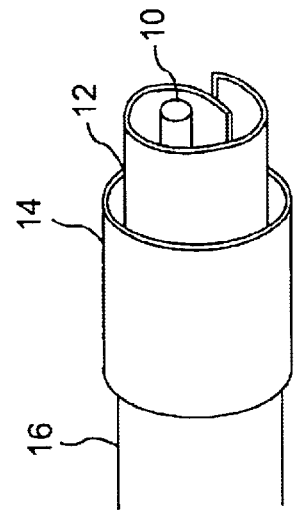
FIGS. 3a, and 3b are a cross-sectional view and a front view of a foil sheet, a stent, and a protective shield according to an embodiment of the invention.
Figure 3A:
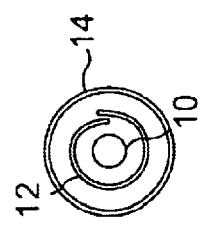

FIGS. 3a and 3b illustrate respective cross-sectional and front views of a device according to another embodiment of the present invention including a catheter for delivery of the foil sheet 12 and stent 10 to the treatment location. To prepare for use, foil sheet 12 is coiled and positioned around the outer surface of stent 10. Both foil sheet 12 and stent 10 are then placed inside catheter 16. Catheter 16 may be any type of conventional catheter which is used to place stents in vessels in a body. A shield 14 for covering foil sheet 12 and stent 10 is preferably located at the end of catheter 16. As the catheter 16 travels through a vessel in the body, shield 14 covers and protects foil sheet 12 and stent 10, to prevent them from getting caught on the internal wall of the vessel and/or from becoming dislodged from their position in catheter 16 and relative to one another, thereby enabling accurate positioning of the stent 10 and foil sheet 12 in the vessel.

Once the stent 10 and foil sheet 12 are located in the desired position, shield 14 is drawn back, such as in the direction of the arrows as illustrated in FIG. 3b. Stent 10 or foil sheet 12 may include a radioopaque material so that it can be accurately located in a patient using conventional x-ray or other radiation scanning devices. Stent 10 is then expanded in any conventional manner, e.g., by inserting and inflating a balloon within the stent. FIG. 4 illustrates a cross-sectional view of an expanded stent 10 and foil sheet 12 located within a vessel according to an embodiment of the invention. Expansion of stent 10 causes foil sheet 12 to contact vessel wall 18. In the embodiment shown in FIG. 4, foil sheet 12 is located between stent 10 and vessel wall 18.

The foil sheet 12 disclosed in the embodiment of FIG. 4 comprises a radioactive material portion 20 and a shielding material portion 22. Shielding material portion 22 may be applied to one side of foil sheet 12 to shield a particular area of the body, thereby reducing or eliminating the radioactive dosage received by that area of the body. According to the embodiment illustrated in FIG. 5, shielding material portion 22 is located on the inner side of foil sheet 12, and adjacent the outer diameter of stent 10, thereby permitting/directing the radiaon outwardly toward the vessel walls. Shielding material portion 22 may be of any conventional material which will shield radioactivity, and preferably is a biocompatable material, such as titanium.

The present invention enables the delivery of a radioactive dose in combination with conventional stents without having to modify the set. The foil sheet 12 may be manufactured to any desired size, thereby enabling its use with any size or type of stent Production costs may be reduced, as foils sheets with radioactive marine may be easier to manufacture and prepare than radioactive stents. Alternative, sheets of radioactive material can be fabrication and, at the time of use, the foil sheet 12 can be cut to the desired size for use with a particular stent.

As illustrated in FIG. 4, placing a foil sheet 12 adjacent the outer diameter of stent 10 enables the foil sheet 12 to be adjacent to the vessel wall. The amount and/or intensity of radioactive material used with the foil sheet 12 may be less than would be required if the radioactive material were incorporated directly into the stent 10 since as the distance over which the dosage must be delivered is less. This results in reduced production costs as less radioactive material is require. Additionally, reducing the amount and/or intensity of the radioactive material may reduce the dosage received by issue in the vicinity of the treatment area, where little or no dosage is desired.

Figure 7:
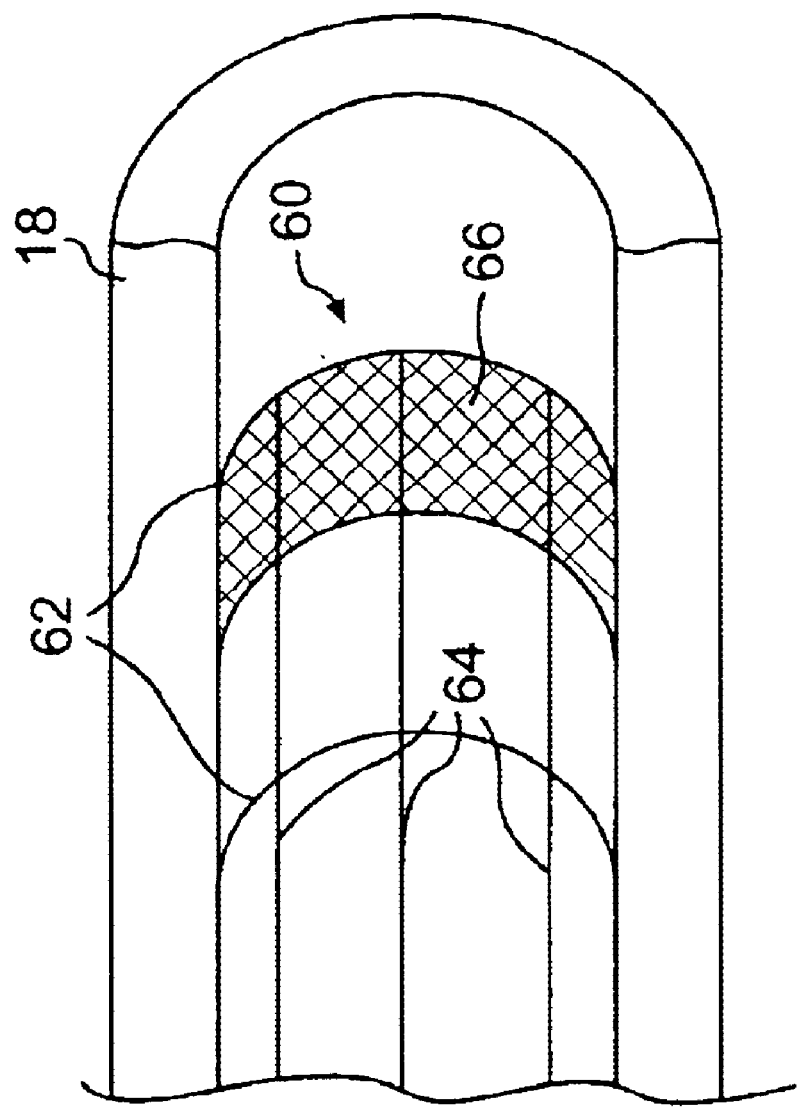
FIG. 7 is a cross-sectional view of another embodiment of the present invention showing an expanded foil sheet.

FIG. 7 illustrates a cross-section view of a device for irradiating and/or delivering drugs according to another embodiment of the invention. A foil sheet 60 is located within a vessel 18, such as a blood vessel. Foil sheet 60 may be similar to foil sheet 12 in that foil sheet 60 may be originally fabricated as a flat sheet of material, and then coiled for placement within the vessel. In this embodiment of the invention, foil sheet 60 is designed to conform with an area of the body in the treatment zone. For example, foil sheet 60 may be made from a flexible material and therefore be able to take on the shape of the body part directly adjacent foil sheet 60 in the treatment zone. Alternatively, foil sheet 60 may be coil which can be expanded to conform to the inner diameter of tubular body parts such a vessels which may be treated with radioactive material.

According to a specific embodiment of the invention, foil sheet 60 comprises vertical supports 62, horizontal supports 64, and a film material 66. Vertical supports 62 and horizontal supports 64 are configured to provide support for film material 64 and enable the foil sheet 60 to hold its shape when expanded. In the example disclosed in FIG. 7, vertical supports 62 and horizontal supports 64 are configured at approximately ninety degree angles to each other, thereby providing a screenlike support for film material 66. Alternative configurations of supports 62, 64 are also possible within the scope of the invention depending upon the specific needs for a particular application.

Film material 66 may be attached to horizontal supports 62 and vertical supports 64 via any conventional manner, such as heat setting, welding, soldering, electroplating, electroless plating, adhesives, staples, melt bonding or any other suitable manner of attachment known to a skilled person. Horizontal supports 62, vertical supports 64 and film material 66 may be fabricated using the same materials used to fabricate the foil sheet 12 of the present invention.

As illustrated in FIG. 7, foil so 60 is a permanent implant that is expandable to substantially conform to the contours of the inner wall of the vessel 18, such as the inner wall of a blood vessel. Foil sheet 60 does not provide any support for the vessel 18. The expansion of foil sheet 60 allows for foil sheet 60 to conform to the vessel 18, thereby fixing the foil sheet 60 into a position with the vessel 18, without providing any support for the vessel 18. This is important since this method of positioning the foil sheet 60 combines the advantages of delivering the radiation dose as close to the site to be treated as possible while at the same time minimizing trauma to the treatment zone which may otherwise be caused by placement of the radioactive material therein.

Attentively, a radioactive or therapeutic material may be incorporated into one or more of the supports 62, 64. No film material or foil sheet need be employed in this embodiment. In use, the supports 62, 64 are expanded to conform to a portion of the treatment zone, preferably without significantly deforming the treatment zone or causing trauma. Expansion of supports 62, 64 results in the radioactive or therapeutic material being positioned in the desired location for the treatment.

Figure 8A:
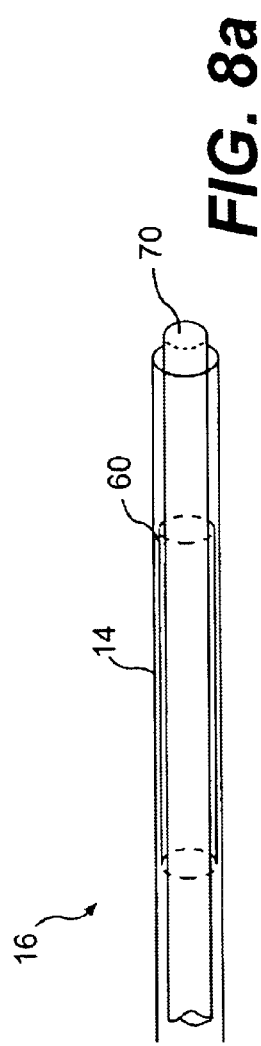
FIGS. 8a-8c are cross-sectional views of a foil sheet, a support rod, and a protective shield according to another embodiment of the invention.
Figure 8B:
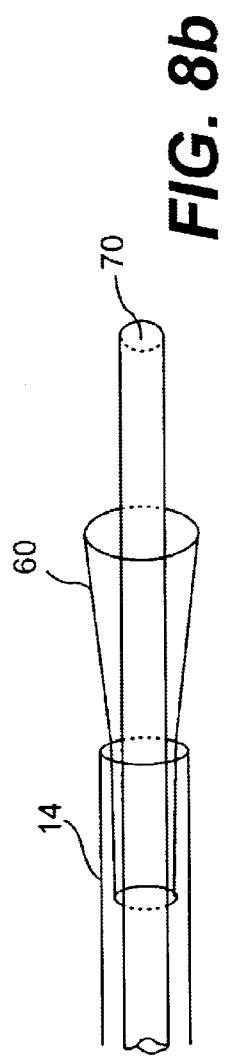
Figure 8C:
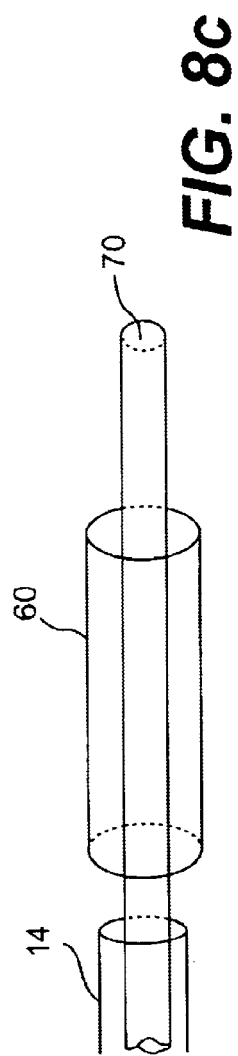

FIGS. 8a-8c illustrate a manner of delivering a foil sheet 60 for insertion into a vessel 18. A foil sheet 60 is placed within a catheter 16. According to an embodiment of the invention, catheter 16 may be limited to the catheter used in connection with foil sheet 12 and stent 10 as illustrated in FIGS. 3a and 3b. Catheter 16 includes a shield 14 for covering foil sheet 60. A support rod 70 is located within shield 14 of catheter 16, and foil sheet 60 is located outside support rod 70, but within shield 14. As catheter 16 travels through a vessel, shield 14 covers and protects foil sheet 60. According to an embodiment of the invention, foil sheet 60 may automatically expand on its own.

As Illustrated in FIG. 8b, once the catheter 16 has located foil sheet 60 at an appropriate location within a vessel, shield 14 is drawn back, such as in the directions of the arrows illustrated in FIG. 8b. As with stent 10 and foil sheet 12 combination described above, foil sheet 60 may include a radioopaque material so that it can be accurately located with a patient using convention x-ray or other radiation scanning devices. According to an embodiment of the invention, where foil sheet 60 is self-expanding, foil sheet 60 begins to expand as shield 14 is drawn back. FIG. 8c illustrates foil sheet 60 fully expanded within a vessel, while support rod 70 is located within foil sheet 60. As catheter 16 is removed, support rod 70 is also removed, thereby leaving foil sheet 60 within the vessel.

According to another embodiment of the invention, foil sheet 60 may be expandable, but not expand on its own. Support rod 70 of the catheter 16 may then be replaced with an expandable component, such as a balloon. The expandable component expands after shield 14 has been drawn back, thereby conforming foil sheet 60 to the contours of the inside wall of the vessel.

Other embodiments, uses and advantages of the present invention will be apparent to those skilled in the art from consideration of the specification and practice of the invention disclosed herein The specification and examples should be considered exemplary only. The intended scope of the invention is only limited by the claims appended hereto.

What is claimed is:

1. A device for delivering a dose of radiation comprising:

a stent for insertion into a vessel of a body comprising a generally tubular structure having an inner diameter and an outer diameter; and a foil sheet formed into a coil and located adjacent the stent without being attached to the stent, wherein the foil sheet comprises a radioactive material and said foil sheet is radially expandable by at least partially uncoiling said coil.

2. The device of claim 1, wherein the foil sheet is located adjacent the outer diameter of the stent.

3. The device of claim 2, wherein the stent and the foil sheet are radially expandable, such that radially expanding the stent causes the foil sheet to radially expand and contact the vessel.

4. The device of claim 1, wherein the radioactive material is palladium-103.

5. The device of claim 1, wherein the radioactive material is carrier free palladium-103.

6. The device of claim 5, wherein said foil sheet provides substantially no support to the area of the body to which it conforms when it is conformed to the area of the body in the treatment zone.

7. The device of claim 6, wherein the foil sheet is an expandable device capable of expanding to provide a device of a predefined geometric shape which conforms to an area of the body in the treatment zone while permitting flow of fluids therethrough.

8. The device of claim 7, wherein the foil sheet further comprises a dosage of a drug.

9. The device of claim 7, wherein the foil sheet further comprises a mechanical attachment for securing the foil sheet in position in the treatment zone.

10. The device of claim 9, wherein the mechanical attachment is selected from the group consisting of adhesives and suturing.

11. The device of claim 7, further comprising a support which assists in conforming the foil sheet to an area of the body and maintaining the foil sheet in position in the treatment zone during treatment.

12. The device of claim 7, wherein the foil sheet is positioned in the treatment zone adjacent to the outer diameter of the stent.

13. The device of claim 12, wherein the stent and the foil sheet are radially expandable, such that radially expanding the stent causes the foil sheet to radially expand and conform to an area of the body.

14. The device of claim 1, wherein the foil sheet is a woven screen.

15. The device of claim 1, wherein the foil sheet further comprises a bioabsorbable material that can be absorbed into the body.

16. The device of claim 1, wherein the foil sheet includes two sides, and the foil sheet has a titanium coating on at least one of the sides of the foil sheet.

17. The device of claim 1, wherein the foil sheet further comprises a dosage of a drug.

* * * * *